United States Patent

Raehse et al.

[11] Patent Number: 5,858,169
[45] Date of Patent: Jan. 12, 1999

[54] PROCESS FOR THE SIMPLIFIED SEPARATION OF MULTICOMPONENT MIXTURES OF AT LEAST PARTLY ORGANIC ORIGIN

[75] Inventors: Wilfried Raehse, Duesseldorf; Johann-Friedrich Fues, Grevenbroich; Karl-Heinz Buettgen, Kerpen; Ovidiu Dicoi, Monheim, all of Germany

[73] Assignee: Henkel Kommanditgesellschaft auf Aktien, Duesseldorf, Germany

[21] Appl. No.: 649,658

[22] PCT Filed: Nov. 15, 1994

[86] PCT No.: PCT/EP94/03786

§ 371 Date: May 23, 1996

§ 102(e) Date: May 23, 1996

[87] PCT Pub. No.: WO95/14520

PCT Pub. Date: Jun. 1, 1995

[30] Foreign Application Priority Data

Nov. 24, 1993 [DE] Germany .......................... 43 40 093.0

[51] Int. Cl.⁶ ................................. B01D 1/14; B01D 3/34
[52] U.S. Cl. ...................... 159/48.1; 159/4.01; 159/16.3; 203/40; 203/43; 203/49
[58] Field of Search ...................... 203/40, 43; 159/4.01, 159/16.3, 48.1; 528/501

[56] References Cited

U.S. PATENT DOCUMENTS

| | | | |
|---|---|---|---|
| 2,759,967 | 8/1956 | Cash et al. | 560/98 |
| 3,907,709 | 9/1975 | List et al. | 252/453 |
| 4,090,922 | 5/1978 | Bauer et al. | 203/48 |
| 4,143,072 | 3/1979 | Hetzel et al. | 260/573 |
| 4,393,203 | 7/1983 | Mao et al. | 536/124 |
| 4,443,634 | 4/1984 | Ziegenhain et al. | 568/621 |
| 4,458,957 | 7/1984 | Greener | 308/187.1 |
| 5,431,780 | 7/1995 | Raehse et al. | 159/48.1 |

FOREIGN PATENT DOCUMENTS

| | | |
|---|---|---|
| 015 739 | 4/1983 | European Pat. Off. |
| 092 876 | 11/1983 | European Pat. Off. |
| 283 862 | 9/1988 | European Pat. Off. |
| 910 829 | 6/1946 | France . |
| 1021887 | 2/1953 | France . |
| 2253542 | 7/1975 | France . |
| 976 413 | 7/1963 | Germany . |
| 30 44 488 | 7/1982 | Germany . |
| 34 47 867 | 7/1986 | Germany . |
| 40 30 688 | 4/1992 | Germany . |
| 42 04 035 | 8/1993 | Germany . |
| 42 04 090 | 8/1993 | Germany . |
| 42 06 050 | 9/1993 | Germany . |
| 42 06 495 | 9/1993 | Germany . |
| 42 06 521 | 9/1993 | Germany . |
| 42 08 773 | 9/1993 | Germany . |
| 42 09 432 | 9/1993 | Germany . |
| 42 34 376 | 4/1994 | Germany . |
| 4237934 | 5/1994 | Germany . |
| 5 414/81 | 1/1981 | Japan . |
| 9315816 | 8/1993 | WIPO . |

OTHER PUBLICATIONS

Die Praxis des organischen Chemikers (1948). . .

(List continued on next page.)

Primary Examiner—Tae Yoon
Attorney, Agent, or Firm—Ernest G. Szoke; Wayne C. Jaeschke; Real J. Grandmaison

[57] ABSTRACT

A process for separating a multi-component mixture containing solid or liquid organic components by treating the mixture with a gaseous entraining agent comprising a superheated carrier fluid containing a lower monohydric alcohol or a lower monohydric alcohol and water to cause constituents of the multi-component mixture to become entrained in the gaseous entraining agent, and separating the gaseous entraining agent containing constituents of the multi-component mixture from the multi-component mixture.

27 Claims, 4 Drawing Sheets

OTHER PUBLICATIONS

"Grundlagen der Einphasen–und Merphasenströmungen" in Grundlagen der Chemischen Technik, 1971, pp. 308–323 (reference to follow)

Lefebvre, "Atomization and Sprays", Hemisphere Publishing Corp, NY, 1989 pp. 10–20 (reference to follow)

Chemical Engineering, vol. 2, Unit Operations (2nd Ed, 1968) Pergamon Press, Oxford/NY, 602–617 (reference to follow).

Perry et. al., "Chemical Engineering Handbook" (5th Eddt, 1976), MacGraw–Hill Book co. NY Phase Dispersion/Liquid–in Gas Dispersions, pp. 18–61 to 18–65 (reference to follow).

Üllmans Enzyklopädie det technischen Chemie (1976), pp. 479–486 (reference to follow).

Grundlagen der Einphasen–und Merphasenströmungen pp. 308–323(reference to follow).

PROCESS FOR THE SIMPLIFIED SEPARATION OF MULTICOMPONENT MIXTURES OF AT LEAST PARTLY ORGANIC ORIGIN

BACKGROUND OF THE INVENTION

1. Field of the Invention

The invention describes proposals for intensifying and/or simplifying the separation of multicomponent mixtures of at least partly organic origin using a stream of carrier gas to simplify the removal of the more readily volatile constituents of the mixture. Accordingly, the principle behind the process according to the invention is based on purification steps which may be classified under the heading of "treatment with steam (steaming)". However, the working principle according to the invention differs from this in the choice of the carrier gas stream which is described in detail in the following in regard to its composition and the operating conditions applied and which is not formed by steam, but instead by a carrier gas of at least partly organic origin. Nevertheless, the measures known to the expert from steam distillation may be widely applied.

2. Discussion of Related Art

The principles of steam distillation for separating multicomponent mixtures and, in particular, for purifying useful materials or mixtures of useful materials of at least partly organic origin are part of established chemical knowledge, cf. for example L. Gattermann "Die Praxis des organischen Chemikers", 33rd Edition (1948), Walter De Gruyter & Co. Verlag, pages 26 to 28 and 252. The principles described herein for laboratory practice are used in various technical applications in such diverse forms that it is only possible here to refer briefly to a number of characteristic applications.

The purification of vegetable or animal fats and oils comprises a multistage treatment in which steaming of the prepurified material is usually carried out as the last stage. An important technical objective of this stage is deodorization of the prepurified material. Unwanted and, in particular, olfactorily troublesome impurities often present in traces only are separated from the useful material or mixture of useful materials by distillation with steam. However, this steaming stage may also be used as a distillation aid, for example to facilitate the removal of short-chain fatty acids from the natural fats and oils. The relevant literature is represented, for example, by "Ullmanns Enzyklopädie der technischen Chemie", 4th Edition, Vol. 11 (1976), pages 479–486; Kirk-Othmer "Encyclopedia of Chemical Technology", 3rd Edition, Vol. 9 (1980), pages 816–820 and E. Bernadini "Vegetable Oils and Fats Processing" in "Oilseeds, Oils and Fats", Vol. 11 (1983), InterstampaRome, Chapter VII, pages 221–251 (Deodorization of Fats and Oils). The industrial purification processes described herein using the principle of steam distillation or steaming operate in vacuo and at high temperatures. For example, steaming is carried out under a pressure of 2 to 30 mbar and at a temperature of 150° to 290° C. The amount of steam used and the treatment time are determined by the particular type of process selected. Batch processes, semicontinuous processes and continuous processes are known. Whatever the type of process, the steam is passed in finely dispersed form through the melted and flash-heated fat or oil. In semicontinuous and continuous processes, other aids may also be provided to enlarge the surface between the steam and the oil phase to be purified. Packed or filled columns in particular are described in this regard. In the column, the liquid to be purified is exposed to the steam passing through with a spread and, hence, enlarged surface.

Another typical industrially significant application for purification by steaming is the removal of residues based on ethylene oxide and/or propylene oxide from reaction products which have been produced by ethoxylation and/or propoxylation of organic compounds containing at least one active hydrogen atom. Compounds of this type are widely used, for example, as nonionic surfactants or as intermediate products for the production of anionic surfactant compounds. They are used, for example, in the field of detergents and cleaning formulations and also on a large scale in the field of cosmetics or pharmaceutical auxiliaries. From their production, the reaction products initially accumulating contain traces of ethylene oxide and/or propylene oxide and of unwanted secondary reaction products, such as dioxane. The removal of these residual materials from the alkoxylated derivatives is described in legislation and is an essential step of the production process. The steam distillation or rather steaming of the reaction products initially accumulating to remove the unwanted impurities is the process step industrially applied in practice, cf. for example EP-A1-0 283 862, DE-A1-34 47 867, U.S. Pat. No. 4,143,072 and the literature cited therein.

According to one modification of the above-described working principle, however, the useful materials or mixtures of useful materials to be purified may advantageously be heated in vacuo and at the same time concentrated by evaporation and purified by the principle of steam distillation. The use of additional, optionally superheated steam for this purpose is known from the prior art. If desired, the impurity-free products of relatively low water content thus obtained may be subsequently converted back into a water-containing preparation, cf. for example DE-A1 30 44 488 which describes a process for the production of ether sulfates of reduced dioxane content.

It is also known that the deodorization and/or removal of unwanted impurities can be carried out using non-condensable gas phases as a distillation aid. The preferred auxiliary for this purpose is gaseous nitrogen which may be used to facilitate removal of the more highly volatile constituents from mixtures, cf. for example JP-AS-5414/81. In this document, polyalkylene glycol derivatives (for example for use as emulsifiers, lubricating oils, starting materials for plastics, detergents, cosmetics and the like) are subjected to purification and deodorization by the introduction of gaseous nitrogen or steam into the liquid material to be purified at around 30 torr and at a temperature of 90° to 100° C. It has also recently been proposed to use non-condensable inert gases, especially nitrogen, instead of steam as a stripping aid in the above-mentioned deodorization of edible oils and/or fats, cf. for example EP-A2-015 739.

U.S. Pat. No. 4,443,634 describes a process for the purification of fatty alcohol polyglycol ethers, in which the material to be purified is sprayed into a chamber from which the impurities are removed in vaporous form. Corresponding mixtures containing less than 2% by weight of the impurities to be removed, based on the liquid starting material, are described as the material to be purified. The material to be purified is said to be sprayed in an inert atmosphere, the pressure having to be selected so that droplets between 50 and 1,000 μm in diameter are formed. These droplets are said to be exposed to the inert gas atmosphere for a matter of seconds and then collected. Nitrogen, helium and argon are mentioned as inert gases. The impurities to be removed by this spray treatment are, in particular, ethylene oxide, propylene oxide, dioxane, water and alcohol. Spraying of the liquid phase into the space filled with inert gas may even be carried out several times in succession.

In their earlier German patent applications P 42 37 934.2 and P 43 07 115.5, applicants describe important improvements for purifying organic materials with superheated steam. The first of these two earlier patent applications describes a process for improving the purity and, in particular, color and odor of useful materials or mixtures of useful materials from the field of wetting agents, detergents and/or cleaning formulations (starting material), which is characterized in that an impurity-laden starting material is treated with superheated steam, bleaching agents optionally being used in the starting material to produce improvements in color. The impurity-laden starting material is preferably subjected to the treatment with superheated steam in fine-particle form and especially in admixture with water and, if desired, is at least partly dried at the same time. The treatment with superheated steam is best carried out in a spray zone and/or a fluidized bed.

The second of the earlier applications cited above describes a process for intensifying and/or accelerating the distillation-based separation of multicomponent mixtures of at least partly organic origin using a stream of steam to facilitate the removal of steam-volatile components of the starting material (steaming) which is characterized in that a starting material liquid under the treatment conditions is steamed in finely sprayed form. The treatment with steam is preferably carried out with steam superheated at the operating pressure. In one particularly important embodiment, the liquid phase to be purified is sprayed using a propellent gas. In one particularly advantageous embodiment, multicomponent spray nozzles are used. In the most important embodiments of this technical teaching, steam and, in particular, superheated steam is at least partly used as the propellent gas.

The disclosures of the two earlier German patent applications P 42 37 934.2 and P 43 07 115.5 cited above are hereby specifically included as part of the disclosure of the present invention. The principles described in those applications are also applicable to the teaching of the present invention as described in the following, the modification according to the invention being that a selected superheated vapor phase of at least partly organic origin is used instead of superheated steam as the gaseous entraining agent.

Before the teaching according to the invention is discussed in detail, applicants would first like to mention a totally different industrial application of the principles of steam distillation. It is known that, quite generally, difficult distillation-based separations can be made easier by applying the principle of steam distillation. For example, the removal of unreacted fatty alcohol components in the production of nonionic surfactants from the class of alkyl polyglycosides (APG) is described in EP-B-0 092 876 and later corresponding applications. Distillation of the APG-containing crude product is carried out in vacuo in a thin-layer evaporator. Removal of the free fatty alcohol to be distilled off can be promoted by exposing the starting material spread widely over the inner surface of the thin-layer evaporator to the stream of steam passing through with its enlarged surface.

DESCRIPTION OF THE INVENTION

By contrast, the present invention in a first embodiment relates to a process for the simplified separation of a multicomponent mixture containing solid and/or liquid organic constituents (hereinafter also referred to as the "starting material") by the treatment thereof with a gaseous entraining agent which is delivered as the superheated vapor phase to the separation stage—based on the operating conditions thereof—and which is removed again laden with parts of the starting material. In the description of the present invention, this superheated steam phase used as entraining agent is also referred to as the superheated carrier fluid (SHCF).

The teaching according to the invention utilizes the process simplifications for separating multicomponent mixtures known from steam distillation. According to the invention, however, lower monohydric alcohols or mixtures thereof with water in the form of the superheated vapor (or gas phase, based on the operating conditions of the separation stage) are used as entraining agents or superheated carrier fluids (SHCF's) as defined above. Preferred alcohols for the SHCF in the content of the teaching according to the invention are primary alkanols containing 1 to 5 carbon atoms and, more particularly, 1 to 3 carbon atoms. Particular significance is attributed to the use of methanol and/or ethanol as the SHCF.

The lower monohydric alcohols as such may preferably be used as the SHCF. As already mentioned, however, the teaching according to the invention additionally encompasses mixtures of these alcohols with water, the alcohol component predominating in important embodiments. However, the use of alcohol/water mixtures with a predominant water content also falls within the scope of the teaching according to the invention, as will be discussed in detail hereinafter.

Basically, the transfer of material between the starting material of at least partly organic origin to be purified on the one hand and the alcohol-based entraining agent superheated under operating conditions on the other hand may be carried out in any technological form. General specialist knowledge may be applied in this regard also. Solid starting materials are preferably subjected to the process according to the invention in sufficiently fine-particle form, more particularly in the form of a flowable solid material. In one particularly important embodiment, however, the multicomponent mixture to be worked up is used in the form of flowable preparations which are liquid under the operating conditions and the multicomponent mixture to be separated is exposed to the gaseous superheated alcohol or alcohol/water phase with an enlarged surface. In one particularly important embodiment, this is done by spraying the liquid phase to be purified in a spray zone, more especially using a propellent gas. In the most important embodiments of the invention, the alcohol-based SHCF phase as defined above is at least partly used as the propellent gas.

In further embodiments, the invention relates to the application of this process in various technological fields. In by far the majority of these applications, the SHCF phase is used as a distillation aid in the separation of at least partly low-volatility mixtures of organic origin. Thus, the SHCF phase may be used in particular to improve the purity of useful materials and mixtures of useful materials of vegetable and/or synthetic origin, more especially for purifying fats and/or oils, for example for their use as foods, and of components from the field of cosmetics, wetting agents, detergents and/or cleaning formulations and also pharmaceutical auxiliaries.

In one particularly important embodiment, the process according to the invention is used for the simplified purification of reaction products from the transesterification of glyceride esters, more especially triglycerides of natural origin, with monohydric alkanols containing in particular 1 to 5 carbon atoms. In this particular application, the use of superheated methanol and/or ethanol as the SHCF stream in the process according to the invention can lead to important process simplifications in the purification of methyl and/or ethyl esters of fatty acids of natural origin which are obtained by transesterification with methanol and/or ethanol from the corresponding glycerides accumulating as natural materials.

So far as this particular application is concerned, it will immediately be clear that lower alkanols and, in particular, methanol and/or ethanol are available as reactants for the transesterification reaction carried out in the reactors now operated on an industrial scale. Considerable circulating streams of these lower monohydric alkanols are used in such reactors. In this embodiment, the teaching according to the invention incorporates in the existing sequence of process steps a purification step in which the SHCF phase, for example based on methanol, is used for the effective separation of the crude product or an insufficiently purified product from the transesterification stage. By "treatment with superheated methanol vapor" in this way, high-quality separation results can be obtained in a technically very simple manner with optimal preservation of the material to be purified. The carrier fluids and amounts of energy used in this separation stage are not lost, but instead may be reintegrated into the process as a whole. This opens up economic and technological possibilities and improvements which, hitherto, had never been regarded as possible.

In one important embodiment, therefore, the teaching according to the invention opens up technologically and economically improved access to industrial products based on natural materials, for example of the type now required as so-called biodiesel in the field of combustion fuels. By applying the working principle according to the invention, the adequate purification of corresponding fatty acid methyl ester mixtures and, in particular, the adequate removal of glycerol from the primary products of the transesterification reaction is facilitated in a hitherto inaccessible manner.

DETAILED DESCRIPTION OF THE INVENTION

A key part of the teaching according to the invention lies in the replacement of the superheated steam hitherto used as entraining agent by the now organically based gaseous or vaporous entraining agent phase. Lower monohydric alcohols or mixtures thereof with water are used under such operating conditions that—based on the particular operating parameters selected—they are present as a superheated vapor phase in the separation stage. This alcohol-based vapor phase performs the function assigned to this working medium in the above-reported knowledge of the facilitated separation of multicomponent mixtures using superheated steam and which lies in particular in the simplified removal of the more volatile components from the starting mixture.

Preferred entraining agents for forming the SHCF's are lower monohydric primary alkanols containing in particular 1 to 5 carbon atoms and preferably 1 to 3 carbon atoms. Particular significance is attributed in this regard to methanol and/or ethanol of which the boiling points under normal pressure are respectively around 65° C. and around 78° C. In the practical application of the new process, n-propanol and isopropyl alcohol (secondary alkanol) with their boiling points under normal pressure of, again, below 100° C. bring working conditions which—based on the boiling characteristics of the entraining agent—bear a strong resemblance to steaming with pure steam. However, the other preferred alcohols of the teaching according to the invention also do not introduce any significant difficulties into the process as far as their boiling characteristics are concerned.

The lower monohydric alcohols and, in particular, the primary alkanols containing 1 to 5 carbon atoms may be used as individual pure substances in the SHCF. However, mixtures of 2 or more alcohols of the described type may also be used as SHCF. For example, the process according to the invention may be carried out as effectively with methanol as the entraining agent as with mixtures of, for example, methanol and ethanol or lower alkanols containing 1 to 3 carbon atoms. Irrespective of this, the invention encompasses the possibility of using water as an additional mixture component for the entraining agent used in superheated form. In this case, too, mixtures of water with individual monohydric lower alcohols or mixtures of water with alcohol mixtures may be present.

More particularly, at least a substantial proportion of the SHCF phase is formed by one or more of the lower alcohols. Thus, the content of lower monohydric alcohols in the SHCF is preferably at least about 10 to 25% by weight. Higher contents of, for example, at least about 30% by weight or at least about 40% by weight are preferred. In the most important embodiments, the lower monohydric alcohol (or the corresponding alcohol mixture) makes up at least about 50% by weight of the SHCF phase. Mixed phases of comparatively low water content can represent particularly preferred embodiments of the invention. In their case, the alcohol content of the SHCF phase is at least about 70% by weight and, more particularly, at least about 80 to 85% by weight and preferably 90% by weight or even higher (based in every case on the SHCF phase).

The use of water in the SHCF phase based on lower alcohols used as the entraining agent can be particularly important when the process according to the invention is applied to water-containing starting materials and, at the same time, drying of these materials is linked to the treatment according to the invention. In this case, water—as a vaporous constituent of the gas phase to be separated from the starting material—becomes part of the optionally circulated SHCF phase. The possibility of leaving part of this water in the optionally circulated superheated vapor phase can lead to process simplifications and even to intensification of the purification process according to the invention. Particular significance may be attributed in this regard to the use of water/alcohol mixtures substantially corresponding to azeotropic mixing ratios of the water/alcohol mixtures in question. General chemical knowledge of these alcohol/water mixtures may be applied in this regard.

The alcohols or alcohol/water mixtures used in accordance with the invention as SHCF are preferably introduced into the separation stage at temperatures which are at least slightly above the boiling point of the highest-boiling component of the particular SHCF used under the operating conditions of the separation stage. Accordingly, it may be advisable to introduce the superheated SHCF stream into the separation stage at a temperature at least about 5° to 10° C., more especially at least about 20° C. and preferably at least about 50° C. above the particular boiling temperature under the operating conditions. Temperatures of the particular SHCF stream of at least 150° to 200° C. above that boiling temperature under the working pressure of the purification stage are often preferred operating parameters. A number of parameters which fall within the scope of general technical knowledge has to be taken into consideration in this regard, including for example the following: the particular choice of the SHCF component(s) selected, the temperature sensitivity of the multicomponent mixture to be treated, the ratio by weight of the SHCF phase to the multicomponent mixture, the particular type of material transfer selected between the starting material to be treated and the superheated SHCF stream and hence, in particular, the residence time of the multicomponent mixture to be treated in the presence of the superheated SHCF and the like.

By suitably selecting the operating conditions just mentioned and taking into account the parameters which are known to the expert in the specific individual case in question or which may readily be determined, the SHCF stream may also assume considerable absolute temperatures. These working temperatures—now detached from the particular boiling temperature of the alkanol under operating conditions—may be up to about 500° C. for example and are preferably in the range from about 80° to 400° C. It is only in the treatment of starting materials sensitive to high temperatures, which contain for example mixture components damaged at temperatures well below 100° C., that the SHCF stream is used at correspondingly reduced temperatures. The separation process according to the invention may also be correspondingly modified through control of the working pressure. The parameters known to the expert from the separation of multicomponent mixtures with superheated steam may be logically applied here. Thus, it will often be desirable—simply in the interests of process simplification—to operate in the vicinity of normal pressure or at only slightly reduced or slightly elevated pressures. Even in industrial installations, reduced pressures or excess pressures deviating from normal pressure by, for example, up to about 150 mbar and preferably by up to about 100 mbar may readily be established. However, far greater deviations of the working pressure have also been achieved for comparable processes on an industrial scale. Thus, the known deodorization of natural fats and oils by steaming in accordance with the relevant literature cited in the foregoing takes place at greatly reduced pressures, for example of around 5 to 20 mbar, but at the same time using high material temperatures which may be well above 100° C., for example in the range from 150° to 270° C. The teaching according to the invention does of course also encompass such extreme combinations of the working conditions of temperature and pressure; the temperature of the superheated SHCF used may substantially correspond to the temperature of the material to be steamed or, if desired, may even be below that temperature. In general, however, it will be preferable to select an SHCF entry temperature which is again above the temperature of the liquid material. It is clear from general specialist knowledge that the embodiment just mentioned—which does of course open up the possibility of introducing additional evaporation energy through the superheated SHCF stream used—provides for optimal process results in regard to acceleration and/or intensification of the proportion of material to be removed.

The minimum temperature of the starting material to be treated in the separation stage is determined by the conditions under which the separation stage is operated and, in particular, by the parameters of operating pressure and boiling temperature of the SHCF at the particular predetermined operating pressure. If the starting material to be purified is delivered to the separation stage with lower temperatures than the boiling temperature of the SHCF under operating conditions, SHCF initially condenses on the starting material with release of heat of condensation until the boiling temperature of the SHCF under operating conditions is established. A corresponding procedure may be appropriate in special cases. In general, however, this comparatively more complex conduct of the reaction is not desirable. The preferred element of the process is applicable in this case, namely that the starting material is delivered to the separation stage at a temperature which corresponds at least substantially to the boiling temperature of the alkanol or alkanol/water mixture used as the SHCF under the working conditions. The actual temperature of the starting material delivered to the separation stage is preferably above that limiting temperature. It may be above that limiting temperature to a comparatively limited extent, for example of up to 50° C. or 100° C. above the limiting temperature in question. However, given sufficiently low volatility of the starting material to be purified in its principal components, considerably higher temperatures may be established for the starting material to be delivered to the separation stage. Specialist technical knowledge may be applied in this regard.

The broad scope of application of the new process principle is evident inter alia from the fact that both liquid and solid starting materials may be subjected to the transfer of material. However, the broad scope of application of the working principle is evident in particular from the diverse technical operating forms which make use of the principle of steaming with superheated steam and of which the basic working principle may be applied to the conditions of working with the SHCF defined in accordance with the invention.

One feature common to all these operating forms is that they attempt to intensify contact between the solid and/or liquid phase on the one hand and the gaseous or vaporous SHCF phase on the other hand. Thus, the treatment of the starting material may be carried out with an SHCF flowing through the separation stage; where solid starting materials are used under the operating conditions, it is possible in particular to use a fluidized bed.

Basically, the principle of achieving an adequate transfer of material between the starting material to be treated and the SHCF is preferably fulfilled in known manner, even where solid starting materials are used. Fine-particle free-flowing solid materials with maximum average particle sizes of up to about 15 mm and preferably with distinctly smaller particle sizes, for example in the range from about 0.5 to 5 mm, can represent preferred forms of a solid starting material for treatment by the process according to the invention. The special technological embodiment of this separation stage again lies within the scope of established specialist knowledge, the above-mentioned treatment in a fluidized bed being only one of the many known possibilities.

The teaching according to the invention is of particular importance for the simplified separation of multicomponent mixtures or starting materials which are liquid under the process conditions. Where corresponding liquid starting materials are used under the process conditions, the transfer of material may be promoted in known manner by bubbling the SHCF stream through the liquid phase in the form of a gas stream. Any known technologies of injecting gas streams, more especially in the lower part of a bulk quantity of the liquid (for example using a plurality of injection nozzles at the bottom of the treatment zone) are suitable.

In preferred embodiments of the teaching according to the invention, however, free-flowing starting materials are exposed to the transfer of material with enlarged surface by spreading the liquid on suitable substrates and/or reducing it by spraying to relatively small particles. It is particularly suitable in this regard to use spray zones, columns optionally containing filling elements, packings and/or other known means to improve spreading of the liquid phase and/or thin-layer evaporators through which the SHCF phases according to the invention flow. In general, the SHCF phase is preferably delivered continuously to and removed continuously from the separation stage while the starting material to be purified may be delivered to the separation stage in batches and/or continuously.

In particularly important embodiments, the teaching according to the invention makes use of the principles which are the subject of applicants above-cited earlier applications P 42 37 934 and P 43 07 115 and of which the working rules have already been included as part of the disclosure of the present invention. In order to complete this disclosure, the key elements, particularly the second of the two applications mentioned above, are briefly summarized in the following. A key element of the teaching of the present invention lies in the following substitution: in the conventional deodorization of fats and oils, for example, on the batch principle, the liquid to be deodorized is initially introduced in the form of a continuous phase while the steam used for steaming is introduced into and passed through the continuous liquid phase to be purified in finely dispersed form, for example through star-shaped or ring-shaped injection systems in a number of outlet openings for the steam. The teaching according to the present invention reverses this working principle. The starting material which flows under the treatment conditions is brought into phase contact with the SHCF-based entraining agent in finely sprayed form. The SHCF generally forms the continuous phase. The result of this reversal is, firstly, a considerable enlargement of the liquid surface per unit volume of the liquid phase to be treated which is crucial to the transfer of material from the liquid phase to the vapor phase. The specific liquid surface crucial to the transfer of material may be enlarged, for example, by a factor of $10^2$ to $10^5$ and, on average, by a factor of $10^3$.

This form of presentation of the liquid phase of the starting material to be treated with its substantially enlarged surface creates the possibility of considerably intensifying and/or accelerating the separation of multicomponent mixtures in accordance with the objective of the present invention. Treatment times of a few hours are now no longer necessary, instead comparable transfers of material to the superheated SHCF phase can be obtained in a matter of seconds. The resulting advantages are quite clear: not only is a very much faster conditioning process possible, the particular exposure of the material to be purified to heat can be safely controlled within predetermined limits. The liquid to be purified may be sprayed by methods known per se. The broad range of relevant technologies on single-component and/or multicomponent nozzles and the associated process techniques and process parameters are available for this purpose. The material to be purified does not have to be kept in the sprayed state for long periods. Conversion of the starting material to be purified into the finely sprayed state and its interaction with the continuous SHCF phase may be repeated several times as required. The previously used SHCF stream and/or corresponding superheated fresh material may be used in the individual spray stages. Repeated spraying may be carried out in a single working unit or in a plurality of separate and successive working units. Even where repeated spraying is applied, exposure times for the starting material to be treated of a matter of minutes will only be exceeded in exceptional cases, if at all.

The process according to the invention may also be carried out in batches or continuously. Examples of characteristic embodiments of the process according to the invention are illustrated in FIGS. 1 to 4 of the accompanying drawings which will be discussed in detail hereinafter.

In the embodiment under discussion, the teaching according to the invention provides in particular for the fluid material to be purified, which is present as a liquid phase at the operating temperature, to be sprayed into a stream of the superheated SHCF and for the liquid phase to be subsequently separated from the SHCF phase. It is intended in this connection to discuss a particular feature relating to particularly preferred embodiments of the teaching according to the invention.

In the embodiment of the invention under discussion here, the liquid phase to be purified is sprayed by means of a propellent gas. Various embodiments of corresponding spray units, more especially spray nozzles, are known in the relevant technology. Reference is made in this connection to the relevant literature, as represented for example by H. Brauer "Grundlagen der Einphasen- und Merphasenströmungen" in GRUNDLAGEN DER CHEMISCHEN TECHNIK, Verfahrenstechnik der chemischen und verwandter Industrien, Verlag Sauerländer, Aarau and Frankfurt am Main (1971), pages 308–323, A. H. Lefebvre "Atomization and Sprays", Hemisphere Publishing Corp., New York (1989), pages 10–20, Chemical Engineering, Vol. 2, Unit Operations (2nd Edition—1968) Pergamon Press, Oxford/N.Y., pages 602–617 and R. H. Perry et al. in "Chemical Engineering Handbook" (5th Edition—1975), MacGraw-Hill Book Co., New York "Phase Dispersion/Liquid-in-Gas Dispersions", pages 18–61 to 18–65.

In particularly preferred embodiments, the process according to the invention is carried out using multicomponent spray nozzles and propellent gas, SHCF phase as defined in the foregoing, i.e. superheated lower alcohols or corresponding alcohol/water mixtures, being at least partly used as the propellent gas in the most important embodiment of the invention. In the essence of the teaching according to the invention under discussion here, the most important embodiment is the use of the superheated SHCF as sole propellent gas for spraying the flowable multicomponent mixture and converting it into the finely dispersed liquid phase. It has been found that, where the propellent gas selected in accordance with the invention is used, the transfer of the components to be removed from the liquid phase to the SHCF phase is intensified to such an extent—presumably as a result of the intensive mixing during spraying—that the cleaning result to be achieved in the particular process cycle can be accomplished in fractions of a second. The mode of operation and advantages of the process according to the invention are thus clearly apparent. Taking into account the particular history of formation of the sprayed droplet as described in the cited literature, which generally includes lamellar spreading of the extremely low-density liquid phase, the intensity of the measure according to the invention with regard to accomplishment of the cleaning result is clearly apparent. The general specialist knowledge of the process engineer for enhancing this effect by selecting suitable multicomponent nozzles may be additionally applied here within the scope of the teaching according to the invention.

In one embodiment, the teaching according to the invention enables virtually the entire SHCF used to be employed as the propellent for spraying the liquid phase to be purified. In important embodiments, however, a predetermined direction of flow of the gas phase is established and maintained in the spray zone through a component stream of the superheated SHCF. Thus, in vertical reaction zones, for example, the countercurrent principle may be applied by spraying the liquid with the SHCF as propellent gas downwards through the reaction zone and, at the same time, directing a component stream of the superheated SHCF upwards in countercurrent to the sprayed material. In overall terms, however, virtually any combinations of co-current and/or countercurrent of the gas and liquid phases may be established in known manner.

The quantity ratios between the material to be purified and the SHCF used as entraining agent are determined by the particular degree of treatment required or desired for the material to be purified with the superheated SHCF. In principle, the quantity ratios familiar to the expert from steaming with superheated steam as the entraining agent apply in this regard. Thus, the particular lower alcohols and/or alcohol/water mixtures used as the SHCF phase may also be employed, for example, in quantities of 0.5 to 20% by weight and preferably in quantities of around 1 to 15% by weight, based on the starting material to be purified, in the purification process modified in accordance with the invention. In many cases, the quantities of alcohol or alcohol mixture to be introduced as the superheated vapor phase are in the range from about 1 to 10% by weight and, more particularly, in the range from about 2 to 5% by weight, again based on the weight of the liquid and/or solid material to be purged. The figures mentioned here apply not only to the use of substantially water-free starting materials, the variation of the process described hereinafter in which water-containing starting materials are used and which includes at least partial drying of the starting material is often carried out with quantities of the SHCF phase in the range mentioned above. However, the use of corresponding quantities of alcohol in the upper range of the figures mentioned and, in particular, even larger quantities of SHCF phase may be useful and/or necessary. The following more detailed observations apply to this particular embodiment of the teaching according to the invention:

The effect of the close relationship between steaming with superheated steam in accordance with the prior art on the one hand and the modification according to the invention using the superheated SHCF stream based on lower alcohols on the other hand is that the teaching according to the invention is also concerned with the field of drying processes in which superheated gas phases are used as the drying gas, more particularly drying processes using superheated steam as disclosed in DE-A 40 30 688 and then in DE-A 42 04 035, 42 04 090, 42 06 050, 42 06 521, 42 06 495, 42 08 773, 42 09 432 and 42 34 376, to which reference is specifically made here.

Accordingly, the process according to the invention is also characterized in that both a substantially water-free starting material and a water-containing starting material may be subjected to the treatment with the SHCF. The water-containing starting material in particular may also be at least partly dried. Both solid, preferably fine-particle starting materials and flowable, more especially completely liquid mixtures with undesirably high water contents, which are to be simultaneously—or even exclusively—dried under control during the treatment according to the invention, may be subjected to the process.

It will readily be appreciated that the teaching according to the invention may be divided into a number of special embodiments. This versatility derives on the one hand from the nature of the starting material, particularly in regard to its water content and the physical characteristics of the water-free useful material or mixture of useful materials under the operating conditions and under normal conditions. On the other hand, the versatility of possible special embodiments derives from the objective of the teaching according to the invention: the teaching according to the invention encompasses not only a conventional separation of multi-component mixtures, but also the drying of the useful material or mixture of useful materials. Accordingly, the equipment or measures to be used in each individual case are largely determined by the particular circumstances prevailing and by the objective to be achieved. Without any claim to completeness, individual characteristic examples are explained in the following:

In a first special embodiment, a starting material which contains water under operating conditions and which is to be dried and at the same time freed from non-aqueous, more especially steam-volatile, impurities under process conditions may be subjected to the treatment according to the invention. As already mentioned, even the removal of water from a water-containing useful material or mixture of useful materials is to be interpreted as distillation-based separation in the context of the teaching according to the invention so that, in this case, the mere acceleration of the drying process by using the superheated SHCF stream can signify a materialization of the teaching according to the invention. However, the special circumstances prevailing in practice make this a special case unlikely to be encountered. Useful materials and mixtures of useful materials in industrial quantities are almost always accompanied by at least traces of impurities which are discharged with the superheated SHCF phase. Thus, useful materials or mixtures of useful materials in the form of aqueous slurries can be worked up in accordance with the teaching of DE-A 42 37 934, but now with the SHCF phase, and at the same time dried on the one hand and deodorized on the other hand.

The teaching according to the invention thus encompasses inter alia a process which is characterized in that solid useful materials or mixtures of useful materials are used in the form of a flowable and sprayable aqueous preparation which, under the conditions of the treatment with the superheated SHCF phase, is capable of forming solids with, in particular, an open-pore internal structure, of which the plasticity and surface tackiness are preferably limited to such an extent that the particles and/or their open internal pores are in no real danger of adhering to one another, even under the conditions of exposure to the SHCF stream. In this connection in particular, it can be important that the useful materials or mixtures of useful materials are processed using water-soluble and/or fine-particle water-insoluble inorganic and/or organic auxiliaries which are preferably solid and non-tacky in their dry state.

However, the teaching according to the invention also encompasses the processing of useful materials or mixtures of useful materials in the form of water-containing preparations of useful materials and mixtures of useful materials which are capable of flow under normal conditions. Examples of materials of this type are water-containing alkoxylation products of starting compounds containing at least one reactive hydroxyl group which are capable of flow under normal conditions. One example of a corresponding product are water-containing preparations of nonionic surfactant components. For most applications of corresponding alkoxylates, the substantially complete removal of the residues of, for example, ethylene oxide (EO) and/or propylene oxide (PO) in the end product and the unwanted cyclic ethers, for example dioxane, formed as secondary products in the alkoxylation reaction is essential. In this case, too, the invention provides in an integral process step for effective removal of these unwanted trace impurities and for the simultaneous drying of the originally water-containing material to a predetermined extent.

The teaching according to the invention encompasses a separation process of the described type which may be carried out in a single stage or even in several stages. In the multistage embodiment of this separation process, the individual process stages may be identically or even differently designed in regard to their technical function. For example, a multistage separation process may comprise 2, 3 or more successive separation stages in which the starting material to be purified is present as a liquid phase under the particular working conditions selected and is sprayed into the separation stage. Equally, however, one stage, for example, may be designed as a spray zone and another stage as a packed column through which the SHCF phase as defined in the foregoing flows.

In one important embodiment of the teaching according to the invention, the SHCF phases based on lower, more especially monohydric, alcohols—or their use in at least one separation stage—are combined with at least one other separation stage designed to make use of the principle which is described in particular in earlier German patent application DE-A-43 07 115 cited earlier on and which is characterized in that steam superheated at the working pressure is used as an alcohol-free separation medium. For this embodiment of the invention in particular, reference is again specifically made to the disclosure of the earlier application mentioned which is hereby included as part of the disclosure of the present invention.

A corresponding combination of separation stages operated on the one hand with a superheated vapor phase based on an alcohol-containing medium and, on the other hand, with a separation gas phase of pure superheated steam can afford important advantages in special cases. Depending on the particular requirements, the separation stage operating with pure superheated steam may precede and/or follow the separation stage using alcohol-based SHCF. The resulting advantages are illustrated in the following examples. If the first separation stage is operated with an alcohol-containing SHCF phase in accordance with the teaching of the invention, a purified end product is obtained which—after condensation of the vaporous residual alcohol in the end product—may contain small residues of alcohol. This is often tolerable. If this is not the case, this residual alcohol content is eliminated in a following separation stage operated with pure steam. The sequence of separation stages may be reversed when residues of condensed moisture are undesirable in the purified end product whereas corresponding residues of a lower alkanol are acceptable.

BRIEF DESCRIPTION OF THE DRAWINGS

The teaching according to the invention is described in detail in the following with reference to FIGS. 1 to 4 of the accompanying drawings which illustrate specific embodiments of the working principle according to the invention. These embodiments are intended purely as examples. Relevant specialist knowledge provides for variations in many respects on the basis of these illustrations to embody the principles characterizing the teaching according to the invention.

DETAILED DESCRIPTION OF THE DRAWINGS

Figure 1:
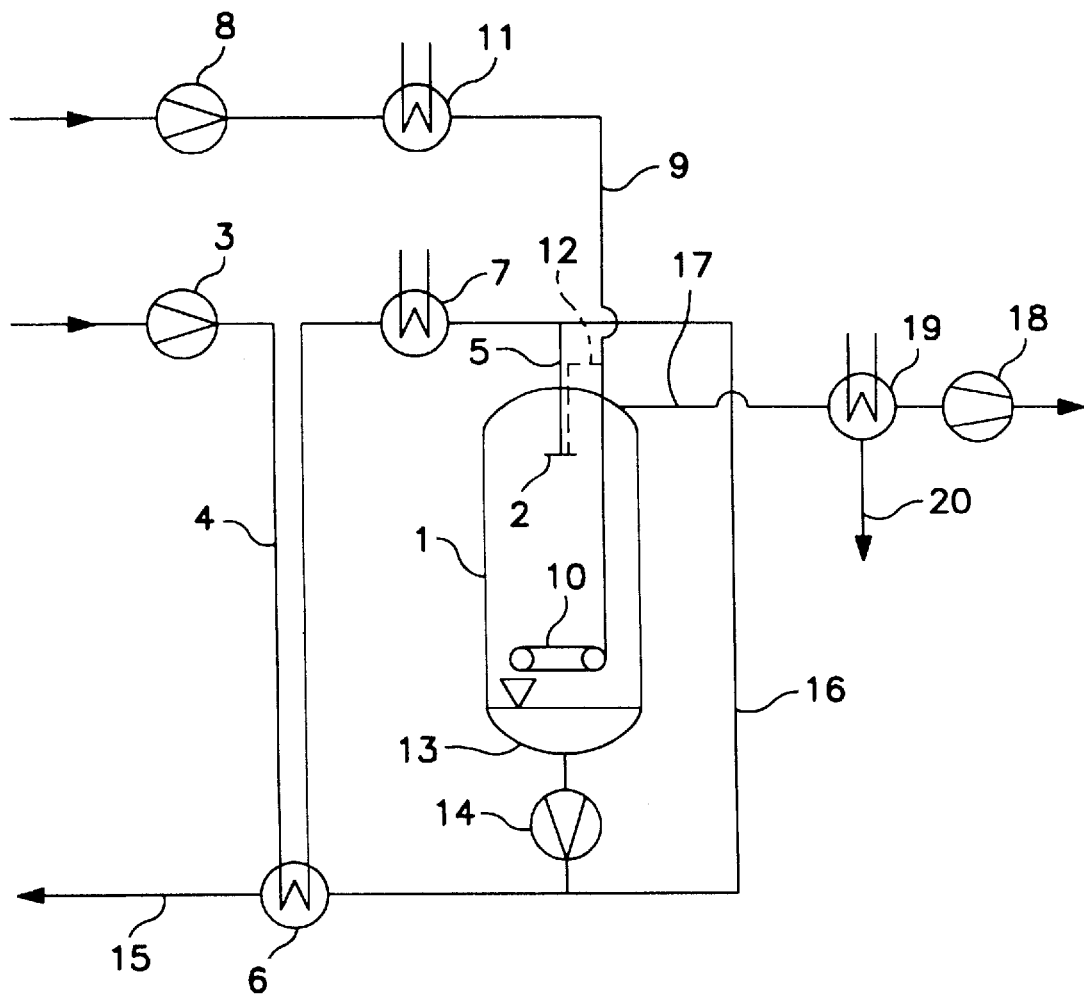

Referring to FIG. 1, a spray system 2 in the form of one or more spray nozzles, optionally multicomponent spray nozzles, is provided in the head part of the boiler 1. The starting material to be treated is delivered to the spray system 2 by the pump 3 through the pipes 4 and 5. The entry temperature of the starting material to be treated is adjusted to the required value by the heat exchanger 6 and the heating system 7. The superheated gas phase used in the form of a vaporous entraining agent is delivered by the pump 8 through the pipe 9 to the distributor element 10 arranged in the lower part of the boiler 1 and flows in countercurrent to the sprayed starting material in the boiler. The required temperature of this SHCF phase as defined in the foregoing is regulated by the preferably indirect heating element 11. At least part of the superheated vapor phase may also be delivered to the spray system 2 in the head part of the boiler 1 through the pipe 12 provided as an alternative and may be used in particular as a propellent gas for the spray process. The liquid product 13 collecting at the bottom of the treatment zone is discharged through the pipe 15 by the pump 14. Alternatively, the treated material may be at least partly recycled to the head of the treatment zone through the pipes 16 and 5. In this way, multiple spraying of the starting material to be purified with the superheated SHCF phase is possible either in batches or even continuously. The SHCF phase laden with the impurities taken up is removed from the boiler 1 through the pipe 17 by means of the fan 18, the superheated vapor passing through the heat exchanger 19. The liquefied part of the vapor stream run off can be removed through 20.

Figure 2:
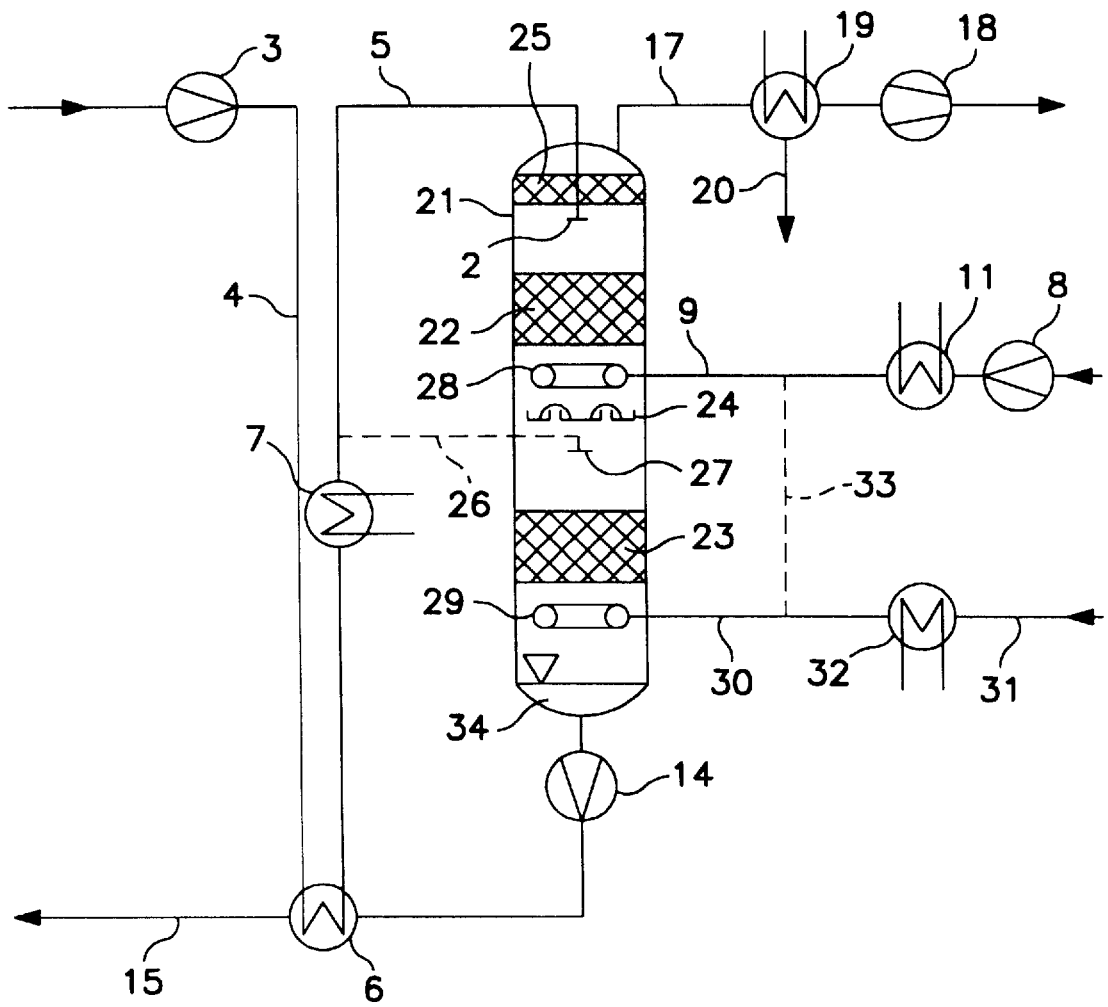

FIG. 2 shows by way of example the possibility of multistage operation, two stages being provided in this particular case. The column 21 is divided into two compartments by the vapor-permeable separation element 24 which, in the drawing, is formed by a bubble tray. The input units 28 and 29 for the superheated SHCF vapor phase are provided in the lower part of these two column sections, the liquid starting material to be treated again being introduced in the head part of the upper column section through a spray system 2. As another possibility, a corresponding input unit for the starting material to be purified is also provided in the head part of the lower column section in conjunction with the spray system 27. Packing elements 22 and 23, for example of the type known and used in the present technology of separation columns for distillation and absorption, are provided in both column sections as an additional phase separation aid. Corresponding packing elements of metal and/or plastic are standard operating elements, in particular for separation by distillation, absorption and desorption in separation columns, cf. for example the brochure entitled "Trennkolonnen für Destillation und Absorption (Separation Columns for Distillation and Absorption)" published by Gebrüder Sulzer AG, Produktbereich Chemtech Trennkolonnen, Winterthur, CH (22.13.06.20–V. 91/100). A demister 25, for example in the form of a correspondingly vapor-permeable packing, is arranged in the head part of the upper column section above the spray nozzles 2.

The starting material to be purified—in the form of a liquid phase—is delivered by the pump 3 through the pipes 4 and 5 to the spray systems 2 of the upper column section. If desired, part of the material is delivered through the pipe 26 to the head part of the lower column section and to the spray nozzles provided there. In this case, too, the heat exchanger 6 and—for definitively controlling the temperature of the starting material—the heating system 7, more particularly an indirect system, are provided in the same way as in FIG. 1.

The superheated SHCF vapor phase is delivered to the upper column section by the pump 8—after passing through the heater 11—through the pipe 9 and the distributor element 28. A superheated SHCF carrier phase is correspondingly introduced into the distributor element 29 through the pipe 31, the heating system 32 and the pipe 30 in the lower column section. Alternatively, part of this superheated entraining agent may also be directly introduced into the bottom part of the upper column section through the pipe 33.

The product 34 purified in several stages which collects at the bottom of the column 21 is discharged by the pump 14 through the pipe 15. The gaseous SHCF entraining agent laden with the impurities taken up is removed at the head of the column through the pipe 17 under the effect of the blower 18. It passes through the heat exchanger 19. The component liquefying therein can be removed through 20.

The procedure illustrated in FIG. 2 is not only an example of the multistage treatment applied in the process according to the invention, it also illustrates the possibility of connecting at least one working stage using the alcohol-containing SHCF phase as defined in the foregoing to another working stage in which superheated steam is used as the entraining agent. In the arrangement shown in FIG. 2, this can be achieved, for example, by introducing the starting material to be treated solely at the head of the column through the spray system 2. The material to be purified thus passes first through the upper purification stage with the packing 22, then through the separating plane 24 and finally through the lower operating stage with the packing 23. Now, for example, the alcohol-containing superheated SHCF phase corresponding to the crux of the teaching according to the invention is introduced in the upper part of the column through the pipe 9 and the distributor element 28 while superheated steam may be introduced as entraining agent in the lower part of the column through the pipe 30 and the distributor element 29. In this way, it is possible to ensure that the purified material 34 collecting at the bottom of the separating column is free from residual alcohol.

Figure 3:
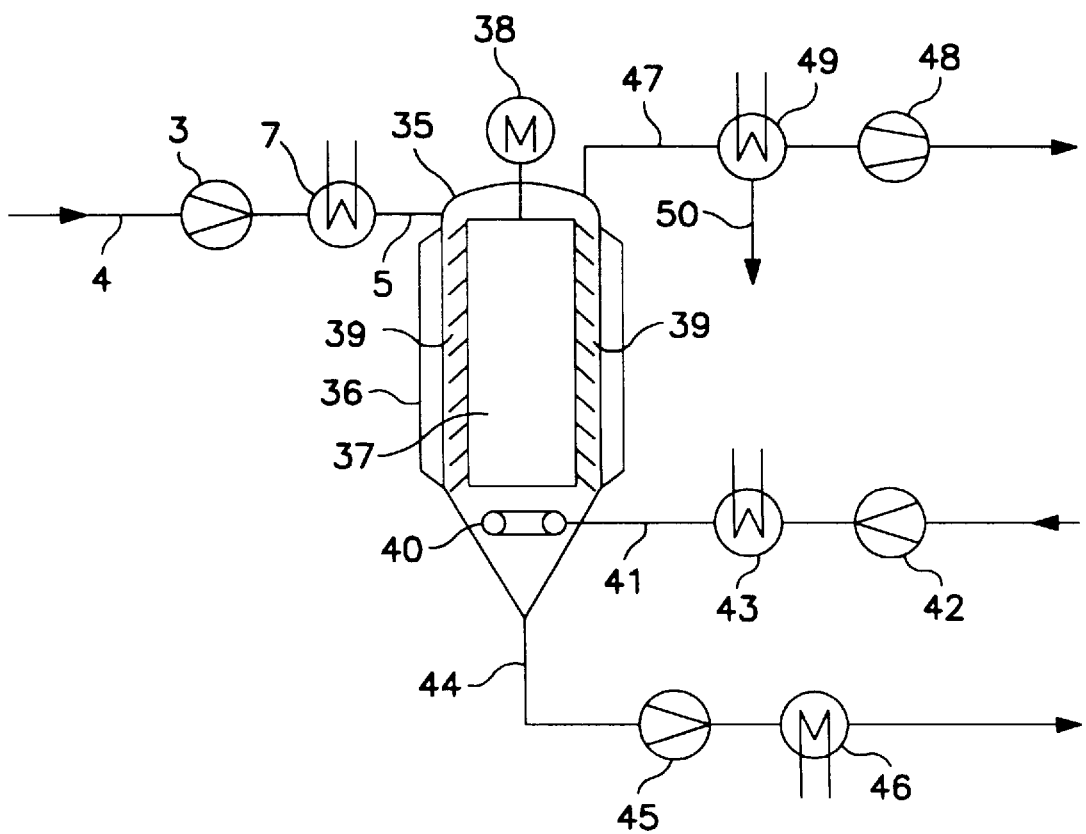

Finally, in FIG. 3, the working principle according to the invention is applied in a thin-layer evaporator 35 with a heatable double jacket 36 and the internally arranged rotor 37 with blades 39 and a drive 38. In operation, the starting material delivered by the pump 3 through the pipes 4 and 5 and heated in the heater 7 is distributed in a thin layer on the inner surface of the thin-layer evaporator and additionally transported downwards by the blades. The superheated SHCF vapor phase flows against this downward movement, being delivered by the pump 42 via the heating stage 43 and the pipe 41 to the distributor element 40 arranged in the lower part of the thin-layer evaporator. The laden entraining vapor phase is removed at the head of the thin-layer evaporator through the pipe 47 by means of the blower 48. The components condensed in the heat exchanger 49 can be removed through the pipe 50. The treated product stream is removed at the foot of the thin-layer evaporator through the pipe 44 by means of the pump 45 and, if desired, is passed through the heat exchanger 46.

In one preferred embodiment, the teaching according to the invention encompasses procedures in which, after separation from the purified material, the laden SHCF phase is at least partly freed from the constituents taken up from the starting material and put to another use. The at least partial recycling of the SHCF phase thus purified to the separation stage(s) is another preferred embodiment for many applications.

Basically, the laden SHCF separation phase can be worked up by any methods known per se to the expert. General specialist knowledge may be applied to this end. It can be particularly useful to apply membrane technology to carry out this secondary working step, cf. for example the textbooks by J. U. I. Dytnerskij "Membranprozesse zur Trennung flüssiger Gemische" VEB Deutscher Verlag für Grundstoffindustrie, Leipzig 1977, and M. Cheryan "ULTRAFILTRATION HANDBOOK", Technomic Publishing Co., Inc., Lancaster/Basel, 1986.

The choice and adaptation of the particular membrane separation process according to the type and characteristics of the membrane selected and the particular technology to be applied is determined by the particular multicomponent mixture to be separated taking general specialist knowledge into account. It is possible both to carry out these membrane separation processes to form liquid product streams and to use pervaporation, in which the phase passing through the membrane is known to accumulate as vapor phase or in the gas phase. The choice of suitable membranes ranges from microfiltration through ultrafiltration and nanofiltration to reverse osmosis. In this case, too, the particular technical measures adopted are determined by the particular characteristics of the multicomponent mixture to be separated.

Figure 4:
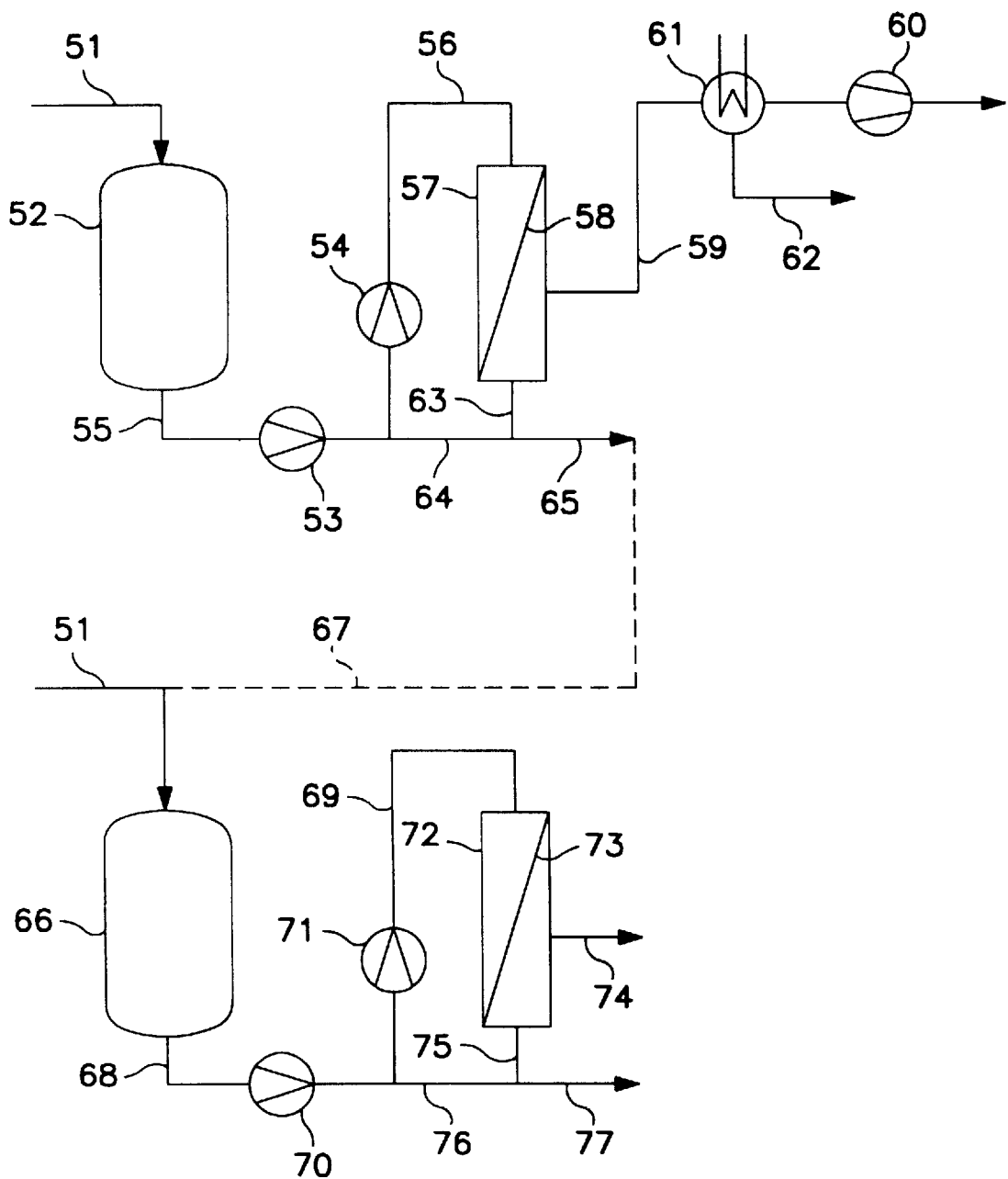

FIG. 4 schematically illustrates possibilities for separating multicomponent mixtures with charged SHCF phases using membrane technology.

The separation aid based on lower monohydric alcohols or mixtures thereof with water charged with impurities in the preceding purification or separation step is introduced as condensate into the holding tank 52 through the pipe 51, removed therefrom by the pumps 53 and 54 through pipes 55 and 56 and introduced into the membrane separation stage 57. Under the working pressure established, the permeate passes through the semipermeable membrane 58 and is removed from the membrane separation stage 57 through the pipe 59 by means of the blower 60. The permeate stream removed can be at least substantially condensed in the condenser 61, so that a purified product stream can be removed through the pipe 62 and put to its intended use. The retentate retained in the membrane separation stage is removed through the pipe 63 and can be at least partly recycled to the separation stage through the pipes 64 and 56. A sufficiently concentrated retentate can be removed through the pipe 65.

A slightly modified embodiment of this separation process, which can also be linked to the hitherto described management of product streams illustrated in FIG. 4, then follows. In this embodiment, SHCF laden with impurities taken up is delivered as liquid phase to the holding tank 66 through the pipe 51. Alternatively or in addition, the retentate 65 removed from the membrane separation stage 57 may also be delivered to the holding tank 66 through the pipe 67. By means of the pumps 70 and 71, the liquefied mixture is delivered through the pipes 68 and 69 to the membrane separation stage 72 with the semipermeable membrane 73 arranged therein. Purified permeate is removed through the pipe 74. Retentate leaves the membrane separation stage through 75 and can be at least partly circulated through 76 and 69. However, enriched retentate is at least partly removed through the pipe 77 and is either put to another use or suitably disposed of.

Certain particularly important applications of the new technology are discussed in the following:

It will always be of particular advantage to apply the purification process according to the invention when this purification with lower alcohols as the SHCF phase readily lends itself to integration in a larger scheme. This is generally the case when, for example, a starting material containing ester groups, more particularly alkanol esters, accumulates in a process step and is to be subjected to subsequent purification. For example, esters of fatty acids or fatty acid mixtures with alkanols, more especially with methanol, ethanol and/or (iso)propanol, are products which accumulate widely on an industrial scale and which generally have to be subjected to a purification step. The corresponding esters of fatty acids based on natural materials and corresponding fatty acid mixtures with lower monofunctional alkanols, more especially methanol and/or ethanol, is mentioned purely by way of example in this regard. Mixtures of this type accumulate on a large scale, for example, in the transesterification of the fatty acid triglycerides, more especially those of natural origin, with the monohydric alcohols. The primary transesterification product contains glycerol and normally requires purification which, nowadays, is mainly carried out by distillation.

In the process according to the invention, purification of the crude transesterification product and, in particular, the separation of glycerol are possible in a single step optionally carried out in several stages. The auxiliary—for example methanol or ethanol—to be used as the SHCF phase is available in sufficient quantities in the transesterification process. According to the teaching of the invention, the purification step is integrated into the process in such a way that the additional consumption of energy and auxiliary chemicals can be reduced to a minimum. However, the purification of esters of fatty acids and relatively long-chain fatty alcohols is another important application for the teaching according to the invention.

However, the use of the separation principle according to the invention is by no means confined to the applications illustrated here. The economy of the separation process may be guaranteed in known manner by at least partly freeing the laden SHCF phase removed from the separation stage from its components taken up from the starting material and preferably recycling it at least partly to the separation stage.

One particularly interesting application is mentioned in the following: for many years, experts have been discussing the use of combustion fuels based on natural oils and fats. Particular significance is now attributed in this regard to the methyl esters of at least predominantly unsaturated fatty acids or fatty acid mixtures which have been referred to for years in the literature as "biodiesel". Hitherto, biodiesel has not been used really successfully in practice. This is due inter alia to problems associated with adequate purification of the methyl esters which, like all chemicals based on natural materials, contain a number of mixture components.

A particular problem in this regard may lie in the adequate separation of the glycerol from the primary product of the transesterification of the triglyceride with methanol. If the glycerol released is not at least substantially freed from the end product, separation phenomena occur in the biodiesel, especially at relatively low temperatures, so that the usefulness of this fuel is limited.

The teaching according to the invention enables the purification stage using superheated methanol as the SHCF phase to be integrated into the process step of biodiesel production and hence the high-purity qualities of the plant-based fuel required to be obtained with minimal additional outlay on energy and auxiliary chemicals.

What is claimed is:

1. The process of separating a multi-component mixture containing solid or liquid organic components comprising treating said mixture with a gaseous entraining agent comprising a superheated carrier fluid containing a lower monohydric alcohol or a lower monohydric alcohol and water to cause constituents of said multi-component mixture to become entrained in said gaseous entraining agent, said treating step being conducted in a spray zone, a fluidized bed apparatus or a thin-layer evaporator, and said superheated carrier fluid being delivered thereto continuously whereas said multi-component mixture is delivered continuously or batch-wise during said treating step, and separating the gaseous entraining agent containing constituents of said multi-component mixture from the multicomponent mixture.

2. A process as in claim 1 wherein said monohydric alcohol is a primary alcohol containing 1 to 5 carbon atoms.

3. A process as in claim 1 wherein said superheated carrier fluid contains at least about 10% by weight of said monohydric alcohol.

4. A process as in claim 1 wherein said superheated carrier fluid is brought into intensive contact with a multi-component mixture comprising solid components having an average particle diameter of up to 15 mm.

5. A process as in claim 1 wherein said treating step is conducted with said superheated carrier fluid at a temperature of at least about 10° C. above the boiling point of the highest boiling point component of said superheated carrier fluid.

6. A process as in claim 1 wherein said multi-component mixture comprises a flowable material under the operating conditions.

7. A process as in claim 1 wherein said multi-component mixture is sprayed co-currently or counter-currently with respect to said superheated carrier fluid during said treating step.

8. A process as in claim 1 wherein said treating step is conducted by spraying said multi-component mixture using said superheated carrier fluid as the propellent gas.

9. A process as in claim 8 wherein said spraying of said multi-component mixture is conducted with multi-component nozzles or atomizing disks.

10. A process as in claim 1 wherein said multi-component mixture is delivered to said treating step at a temperature which at least corresponds to the boiling temperature of the highest boiling component of said superheated carrier fluid during said treating step.

11. A process as in claim 1 wherein said treating step is carried out at ambient pressure or under reduced pressure depending on the volatility of said multi-component mixture and the constituent to be removed therefrom.

12. A process as in claim 1 wherein said treating step is carried out at a temperature of the multi-component mixture which is substantially the same as the temperature of said superheated carrier fluid.

13. A process as in claim 1 wherein the temperature of said superheated carrier fluid is up to about 500° C. during said treating step.

14. A process as in claim 1 wherein said superheated carrier fluid is present in an amount of 0.5% to 20% by weight based on the weight of said multi-component mixture.

15. A process as in claim 1 wherein said multi-component mixture is substantially water-free prior to said treating step.

16. A process as in claim 1 wherein said multi-component mixture contains water prior to said treating step, and optionally, is at least partly dried during said treating step.

17. A process as in claim 1 including repeating said treating step.

18. A process as in claim 1 including treating said multi-component mixture with an alcohol-free superheated steam phase.

19. A process as in claim 1 wherein said multi-component mixture contains ester groups.

20. A process as in claim 1 wherein said multi-component mixture comprises natural materials.

21. A process as in claim 1 wherein said multi-component mixture comprises a reaction mixture from the esterification or transesterification of fatty acids or fatty acid derivatives with alcohols.

22. A process as in claim 1 including removing entrained constituents of said multi-component mixture from said gaseous entraining agent and returning the gaseous entraining agent to said treating step.

23. A process as in claim 1 wherein said superheated carrier fluid consists of a lower monohydric alcohol, and said multi-component mixture comprises a reaction mixture from an esterification or transesterification process containing alkanols.

24. A process as in claim 1 wherein said multi-component mixture comprises a food material.

25. A process as in claim 1 wherein said multi-component mixture comprises a wetting agent or cleaning material.

26. A process as in claim 1 wherein said multi-component mixture comprises a pharmaceutical product.

27. A process as in claim 1 wherein said multi-component mixture comprises a combustion fuel.

* * * * *